United States Patent [19]

Guire et al.

[11] Patent Number: 5,217,492

[45] Date of Patent: Jun. 8, 1993

[54] BIOMOLECULE ATTACHMENT TO HYDROPHOBIC SURFACES

[75] Inventors: Patrick Guire; Shawn G. Dunkirk, both of Eden Prairie, Minn.

[73] Assignee: Bio-Metric Systems, Inc., Eden Prairie, Minn.

[21] Appl. No.: 681,478

[22] Filed: Apr. 3, 1991

Related U.S. Application Data

[60] Continuation of Ser. No. 499,193, Mar. 23, 1990, abandoned, which is a division of Ser. No. 138,226, Dec. 24, 1987, abandoned, which is a continuation-in-part of Ser. No. 108,765, Oct. 15, 1987, Pat. No. 4,973,493, which is a continuation-in-part of Ser. No. 920,567, Oct. 17, 1986, abandoned, said Ser. No. 108,765, is a continuation-in-part of Ser. No. 428,074, Sep. 29, 1982, Pat. No. 4,722,906.

[51] Int. Cl.[5] .............................. A61F 2/02
[52] U.S. Cl. ........................ 623/11; 623/66; 623/1; 427/2; 435/181; 436/501; 604/266
[58] Field of Search .................... 427/2; 435/181; 436/501; 623/1, 2, 11, 66, 901; 604/266

[56] References Cited

U.S. PATENT DOCUMENTS

| | | |
|---|---|---|
| 3,808,113 | 4/1974 | Okamura et al. |
| 3,826,678 | 7/1974 | Hoffman et al. |
| 3,888,833 | 6/1975 | Lednicer et al. |
| 3,955,012 | 5/1976 | Okamura et al. |
| 3,959,078 | 5/1976 | Guire . |
| 4,007,089 | 2/1977 | Smith, III . |
| 4,160,698 | 7/1979 | Miyairi et al. |
| 4,240,163 | 12/1980 | Galin . |
| 4,273,873 | 6/1981 | Sugitach et al. |
| 4,307,071 | 12/1981 | Murray et al. |
| 4,311,573 | 1/1982 | Mayhan et al. |
| 4,326,532 | 4/1982 | Hammar . |
| 4,378,224 | 3/1983 | Nimni et al. |
| 4,378,435 | 3/1983 | Takagi et al. |
| 4,419,444 | 12/1983 | Quash ............................ 435/7 |
| 4,434,150 | 2/1984 | Azad et al. |
| 4,451,568 | 5/1984 | Schneider et al. |
| 4,500,676 | 2/1985 | Balazsa et al. |
| 4,526,714 | 7/1985 | Feijen et al. |
| 4,526,909 | 7/1985 | Urist . |
| 4,530,974 | 7/1985 | Munro et al. |
| 4,536,179 | 8/1985 | Anderson et al. |
| 4,589,881 | 5/1986 | Pierschbacher et al. |
| 4,589,964 | 5/1986 | Mayhan et al. |
| 4,595,632 | 6/1986 | Mayhan et al. |
| 4,605,413 | 8/1986 | Urry et al. ....................... 623/11 |
| 4,657,820 | 4/1987 | Halpern et al. |
| 4,663,233 | 5/1987 | Beavers . |
| 4,678,808 | 8/1987 | Jarrett et al. ................... 525/54.1 |
| 4,715,858 | 12/1987 | Lindstrom . |
| 4,716,122 | 12/1987 | Scheefers . |
| 4,722,906 | 2/1988 | Guire .............................. 436/501 |
| 4,743,258 | 5/1988 | Ikada et al. |
| 4,828,563 | 5/1989 | Müller-Lierheim ............. 623/66 |
| 4,973,493 | 11/1990 | Guire .............................. 623/66 |
| 4,979,959 | 12/1990 | Guire .............................. 623/66 |
| 5,002,582 | 3/1991 | Guire et al. .................... 623/901 |
| 5,002,883 | 3/1991 | Bieniarz et al. ................ 435/181 |

OTHER PUBLICATIONS

Nilsson et al., "Polarographic pO2 Sensors with Heparinized Membranes for In Vitro and Continuous In Vivo Registration", Scan. J. Clin. Lab. Invest., vol. 41, (1982) pp. 557–563.

Bennegard et al., "Material Thrombogenicity in Central Venous Catheterization", Acta Anaesth. Scan., (1982), vol. 26, pp. 112–120.

Guire et al., Glycoconjugate Research, vol. II, (1979), pp. 1051–1054.

Engbers et al., "An In Vitro Study of Adhesion of Blood Platelets onto Vascular Catheters", J. Biom. Mat. Res., vol. 21, (1987), pp. 613–627.

(List continued on next page.)

Primary Examiner—Paul Prebilic
Attorney, Agent, or Firm—Fredrikson & Byron

[57] ABSTRACT

A long chain chemical spacer useful for attaching a biomolecule to a support having a hydrophobic surface, the spacer having a hydrophobic guiding group capable of becoming embedded in the surface, and optionally including a stopping group and/or an attached biomolecule.

11 Claims, 1 Drawing Sheet

GLUCOSE OXIDASE ACTIVITY VS. SPACER CHAIN MOLECULAR WEIGHT

OTHER PUBLICATIONS

Palatianos et al., "Extracorporeal Left Ventricular Assistance with Prostacyclin and Heparinized Centrifugal Pump", Ann. Thor. Surg., vol. 35, No. 5, (1983), pp. 504-515.

Larm et al., "A New Non-Thrombogenic Surface Prepared by Selective Covalent Binding of Heparin Via a Modified Reducing Terminal Residue", Biomat. Med. Dev., Art. Org., 11 (2&3), (1983), pp. 161-173.

Kim et al., Surface Modification of Polymers for Improved Blood Compatibility, CRC Critical Reviews in Biocompatibility, vol. 1, Issue 3, pp. 229-260.

Heyman et al., "Heparinized Polyurethanes: In Vitro and In Vivo Studies", J. Biom. Mat. Res., vol. 19, (1985), pp. 419-436.

Evangelista et al., "Coating of Two Polyether-Polyurethanes and Polyethylene with Heparin-Poly(Vinyl Alcohol) Hydrogel, Biomaterials", vol. 7, May 1986, pp. 206-211.

Hoffman et al., "A New Method for Covalently Coupling of Heparin and Other Glycosaminoglycans to Substances Containing Primary Amino Groups", vol. 117, Carbohydrate Research, pp. 328-331, (1983).

Larsson et al., "Covalent Binding of Proteins to Grafted Plastic Surfaces Suitable for Immunoassays", J. Immuno. Methods, 98, (1987), pp. 129-135.

Ebert et al., "The Anticoagulant Activity of Derivitized and Immobilized Heparins", Eds., Am. Chem. Soc., (1982), pp. 161-176.

Guire, "Photochemical Immobilization of Enzymes and Other Biochemicals", Methods in Enzymology, vol. XLIV, (1976), pp. 280-288, (ed. Klaus Mosbach).

Guire, "Stepwise Thermophotochemical Cross-Linking for Enzyme Stabilization and Immobilization", Enzyme Engineering, vol. 3, (1978), pp. 63-70.

Guire, "Photochemical Coupling of Enzymes to Mammalian Cells", Pharmacological Research Communications, vol. 9, (1977), pp. 131-141.

Price List from Biotechnology Research Enterprises, S.A. Pty. Ltd., dated Nov., 1985, entitled "Photobiotin Acetate".

Katzenellenbagen, et al., Biochem., 13(14):2986-2994 (1974).

Gorman, et al., "Transglutaminase Amine Substrates for Photochemcial Labeling and Cleavable Cross-Linking of Proteins", J. Biol. Chem. 225, 1175-1180 (1980).

BIOMOLECULE ATTACHMENT TO HYDROPHOBIC SURFACES

This application is a continuation of U.S. patent application Ser. No. 07/499,193 filed Mar. 23, 1990 now abandoned, which is a division of Ser. No. 07/138,226 filed Dec. 24, 1987 now abandoned, which is a continuation-in-part of Ser. No. 07/108,765 filed Oct. 15, 1987 now U.S. Pat. No. 4,973,493 which is a continuation-in-part of Ser. No. 06/920,567 now abandoned, said Ser. No. 07/108,765 filed Oct. 5, 1987 now U.S. Pat. No. 4,973,493, is a continuation-in-part of 06/428,074 filed Sep. 29, 1982 now U.S. Pat. No. 4,722,906.

BACKGROUND OF THE INVENTION

Biomolecules—that is, molecules of compounds which engage in a biological activity or are effective in modulating a biological activity—commonly are used in solution or are adsorbed or otherwise attached to solid supporting surfaces such as glass beads. U.S. Pat. No. 3,959,078 refers to the attachment of enzymes to solid surfaces.

Biomolecules can alter the solid or semi-solid surfaces to which they are attached Heparin, for example, can be attached to polyethylene surfaces of a blood bag to provide the surface with anticoagulant properties. Ebert et al.; *The Anticoagulant Activity of Derivatized and Immobilized Heparins*, in Biomaterials: Interfacial Phenomena and applications, Cooper et al., eds., Am. Chem. Soc. 1982, pp.161-176.

Several procedures currently exist for immobilizing synthetic and naturally produced molecules onto solid or semi-solid substrates. The chemistries typically utilized are either highly substrate dependent or result in a significantly reduced activity of the immobilized species. An example of such chemistries include copolymer grafting procedures Larsson, P. H. Johansson, S. G.; Hult, A.; and Gothe, S.: *Covalent Binding of Proteins to Grafted Plastic Surfaces Suitable for Immunoassays;* J. Immuno. Methods, 98, 1987, p-129-135.

The tertiary and quaternary structures of such biomolecules as proteins and polysaccharides have historically been viewed as being "static" in nature. This static view of biomolecular function recently has given way to understanding the dynamic motions of intramolecular structures as a basis for function. Jarplus, M.; McCammon, J. A.: *The Dynamics of Proteins,* Scientific American, April, 1986, p. 42-51. An implication of this understanding is that for optimal activity, proteins and other biomolecules should be immobilized by methods that distort neither the conformation nor the molecular motions of the biomolecules.

In addition to the loss of activity, the conformational distortion that may occur upon immobilization of a biomolecule can give rise to undesired biological responses, especially on implant and medical device surfaces. For instance, increased thrombogenicity or induction of foreign body reactions and rejection following implantation have been reported. When certain macromolecules (e.g. proteins and polysaccharides) encounter previously untreated polymers or other medical device materials, they may adsorb onto these surfaces and undergo alterations in both conformation and activity. Foreign body reactions to soft tissue implants and the thrombogenicity of most polymers involve a cellular level response in the host after a layer of protein has adsorbed onto the device surface. The so called adverse host response may be attributed to the altered macromolecule structure producing an abnormal function when immobilized on the device's surface.

Various plasma proteins undergo slow conformational changes resulting in the loss of secondary structures, such as altered helix or beta-sheet. The denaturation of surface immobilized proteins through these type of changes may render them antigenic. Peters, J. H. and Goetzl, E.: *Recovery of Greater Antigenic Reactivity in Conformationally Altered Albumin,* J. Biological Chem., 224, 1969, p. 2068; Stern, I. J., et al.: *Immunogenic Effects of Materials on Plasma Proteins,* Conf. Proc. Artificial Heart Program, National Heart Institute, 1969, p. 259. The immobilization of some plasma proteins which may produce an altered thrombogenic response. Brash, J. L.; Protein Interactions with Artificial Surfaces, In teraction of the Blood with Natural and Artificial Surfaces, ed. Salzman, E. W., 1981 by Marcel Dekker, Inc., p.39-44.

By spacing biomolecules away from a support, it would be expected that somewhat improved biomolecule activity should be observed. Initial studies indicating the utility of spacer arms have been conducted with heparin. Ebert et al. supra, reported that the bioactivity of heparin could be correlated, to a limited degree, with the length of a spacer holding heparin molecules apart from a supporting surface. Activated partial thromboplastin time was assayed with bovine plasma as an indicator of heparin activity. Heparin was immobilized with hydrophobic aliphatic spacers of varying lengths and produced heparin activity that increased with spacer length. However because of the hydrophobic nature of alkane spacers, the use of longer chains under aqueous physiological conditions would be expected to result in a coiling or doubling back of the spacer molecules, the spacers thus losing their ability to space biomolecules from a solid or semi-solid surface.

SUMMARY OF THE INVENTION

Certain of the practical problems associated with attachment of a biomolecule onto a surface can be avoided by employing a long chain chemical spacer which has two reactive groups separated by a chain length of at least 25 Angstroms when extended. The length of the spacer between the reactive groups is sufficient to space the biomolecule group beyond any substantial adverse interactions associated with the surface to which the spacer is attached. The spacers of the invention generally comply with the following requirements:

1. The spacer may be covalently attached to a support surface and to a biomolecule, and the covalent attachments desirably occur under different predetermined conditions.

2. The reaction conditions for coupling the spacer to a biomolecule are sufficiently gentle as to avoid damaging the biomolecule, and adverse interactions between the biomolecule and the spacer are minimized.

3. Preferably, the spacer contains repeating units such that its length may be adjusted as desired to optimize the specific activities of a given biomolecule.

4. There are no significant bulk physical changes to the surface to which the biomolecule is attached.

The process of the invention involves the treatment of a surface by the immobilization thereon of a biomolecule through the use of a heterobifunctional spacer having two reactive groups thereon, the chemical chain providing a spacing between the groups of at least 25

Angstroms, measured along an extended length of the chain. As used herein, "extended" chain length refers to the straight line distance between two positions along a chemical chain when the chain is stretched to its maximum length consonant with maintaining proper bond angles. For example, propane, $CH_3$—$CH_2$—$CH_3$, exhibits an "extended" chain length between terminal carbon atoms of about 2.5 A (observing a bond angle of 109.5°), whereas the sum of the (carbon-carbon) bond distances along the molecule is about 3.06 A. The distances measured along the spacer chains described herein are all "extended" chain lengths.

The spacers desirably are totally self-contained in that no pretreatment of a target surface to generate bonding groups is required to effect immobilization. An important aspect of the invention is the discovery that adverse substrate/biomolecule interactions can be predictably reduced.

In one embodiment, the invention comprises a long chain spacer for tethering a biomolecule to a surface while avoiding substantial deleterious effect upon the biomolecule by the presence of the surface, the spacer comprising a chemical backbone having two reactive groups attached thereto and separated by a backbone extended chain length of not less than about 25 Angstroms, one such reactive group being capable of forming a covalent bond to a surface in response to a given stimulus, and the other reactive group being capable of forming a covalent bond to a biomolecule. Desirably, one of the reactive groups is responsive to a stimulus to which the other is not. One of the reactive groups preferably is a latent reactive group such as a photoreactive group, and desirably this group is employed to attach the spacer to a surface. The heterobifunctional spacer desirably is more hydrophilic than is the surface to which it is attached (that is, the spacer is more soluble in an employed liquid medium than it is in the support surface); it is postulated that the preferred spacers of the invention hence preferentially stand out from the surface to which they are attached, thereby spacing the biomolecule relatively far from the interfering effects of the surface to which it is tethered by the spacer. Further, the reactive group that attaches to a surface, desirably a photoactive group, preferably is more hydrophobic than the spacer (that is, the group is more soluble in the support surface than is the spacer), and desirably is an aryl group such as an aryl azide or an aryl ketone derivative.

In another embodiment, the invention relates to a method of attaching a biomolecule to a surface in such a manner that the biomolecule is sufficiently spaced from the surface as to escape significant deleterious surface effects. The method comprises reacting a reactive group of a long chain spacer with a given support, and reacting another reactive group carried by the spacer with a biomolecule, the reactive groups being spaced from one another by a chain length of at least 25 Angstroms. The bonds formed to the surface and to the biomolecule are covalent bonds. The reactive groups can be reacted in any order.

In a further embodiment, the invention relates to a support surface, a plurality of biomolecules, and a spacer attaching and spacing the biomolecules to and from the surface, the biomolecule being spaced from the support by a distance, measured along the extended length of the spacer, of at least 25 Angstroms. In this embodiment, the spacer preferably comprises a generally hydrophilic chain having repeating units, such units preferably being oxyalkylene groups such as ethoxy groups or isopropoxy groups.

DESCRIPTION OF THE PREFERRED EMBODIMENTS

A biomolecule is a molecule of a compound which engages in a biologic activity or which is effective in modulating a biological activity. Exemplifying the biocompatible agent may be a growth factor such as endothelial cell growth factor, epithelial cell growth factor, osteoblast growth factor, fibroblast growth factor, platelet derived growth factor, neural growth factor, or angiogenin; an antimicrobial agent such as lysosyme or penicillin; an antithrombogenic agent such as heparin, albumin, streptokinase, tissue plasminogin activator or urokinase; a thrombogenic agent such as collagen; hyaluronic acid, chitosan; and other proteins, carbohydrates and fatty acids, and complex molecule combinations thereof.

A "support surface" refers to the surface of a solid or semi-solid or liquid substance. The surface can be rigid or can be semi-solid such as the surface of a gel. The surface may be a non-rigid, liquid surface such as the surface of a discrete volume of a liquid existing as a discontinuous phase of a multi-phase liquid or liquid/-solid system. The support surface preferably is the surface of a biomaterial as defined below, and commonly is relatively hydrophobic.

A "biomaterial" may be defined as a material that is substantially insoluble in body fluids and that is designed and constructed to be placed in or onto the body or to contact fluid of the body. Vascular grafts, contact lenses, silicone implants and blood bags are examples of biomaterials.

Ideally, a biomaterial will have at least several of the following characteristics:

1. It will not induce undesirable reactions in the body such as blood clotting, tissue death, tumor formation, allergic reaction, foreign body reaction (rejection) or inflammatory reaction.

2. It will have the physical properties such as strength, elasticity, permeability and flexibility required to function as intended.

3. It can be sterilized easily.

4 If used in contact with the body, it will substantially maintain its physical properties and function during the time that it remains implanted in or in contact with the body, whether it be an hour or a lifetime.

As used herein, the treated solid surface of a biomaterial is characterized as "biocompatible" if it is capable of functioning or existing in contact with biological fluid and/or tissue of a living organism with a net beneficial (not net detrimental) effect on the living organism. Long term biocompatibility is desired.

The base material of a biomaterial may be any suitable metal such as polished titanium or stainless steel; a polymer such as polyurethane, polyvinylpyrrolidone, silicone elastomers, polyethylene, polytetrafluoroethylene, polyvinyl chloride, polypropylene, polyolefins, polyesters, polyamides, polyacrylates (including polymethacrylates); minerals or ceramics such as hydroxyapitite; human tissue such as bone, skin and teeth; organic materials such as wood, cellulose and compressed carbon; and other natural and synthetic material such as glass, rubber, wood and the like. Examples of devices which may be provided with biocompatible surfaces in accordance with this invention include vascular graft tubing, dialysis tubing or membranes, blood oxygenator tubing or membranes, ultrafiltration membranes, intra-aortic balloons, blood bags, catheters, sutures, soft or hard tissue prostheses, synthetic prostheses, artificial organs, and lenses for the eye such as contact and intraocular lenses.

A biocompatible "effective" surface is defined as being formed of a plurality of separate biomolecules each covalently linked, through a spacer as defined above, to the support surface of a biomaterial to provide that surface with substantially the same biocompatible characteristics a are possessed by the biomolecule itself. The biomolecules may not densely surround or overlay the support surface as by forming a crosslinked mesh, but may cover the surface in numerous, discrete spots (although this is desirable and may be accomlished), the biomolecules being sufficiently close to one another as to provide the surface with the desired biomolecular characteristics. For example, discrete locations along the surface of vascular grafts may be covered by biomolecules which are cell attachment factors such as fibronectin. The biocompatible effective surface formed at these spots then act as foci for attachment of cells to the thus modified surface.

The reactive groups that are carried by the chemical chain spacers of the invention generally are specific groups that differ chemically from the constituents making up the backbone of the chemical chain of the spacer, and are different from one another. At least one of the reactive groups desirably is a latent reactive group that responds to a predetermined stimulus to covalently bond the spacer to a support surface. Such reactive groups desirably are photochemical groups, the covalent bonding of which is activated by actinic and especially visible or U.V. light radiation. These groups are typified by aryl, alkyl and acyl azides, oxazidines, isocyanates (nitrene generators), alkyl and 2-ketodiazo derivatives and diazirines (carbene generators), aromatic ketones (triplet oxygen generators), aromatic diazonium derivatives and numerous classes of carbonium ion and radical generators. Reference is made to Frederick J. Darfler and Andrew M. Tometsko, chapter 2 of *Chemistry and Biochemistry of Amino Acids, Peptides and Proteins* (Boris Weinstein, ed) vol. 5, Marcel Dekker, Inc. New York, 1978, for further description of photochemically reactive groups. Azidonitrophenyls such as fluoroazido nitrobenzenes, and aromatic ketones form a preferred group due to their stability to chemical reaction conditions in the dark and their susceptibility to activation by light of wave lengths harmless to most biomaterials, to form short-lived reactive intermediates capable of forming covalent bonds in useful yield with most sites on the biomaterial.

Nitrophenylazide derivatives appropriate for use as photochemically reactive groups for the most part can be derived from fluoro-2-nitro-4-azidobenzene, and include 4-azido-2-nitrophenyl ("ANP") -4-amino-butyryl, ANP-6-aminocaproyl, ANP-11-aminoundecanoyl, ANP-glycyl, ANP-aminopropyl, ANP-mercaptoethylamino, ANP-diaminohexyl, ANP-diaminopropyl, and ANP-polyethylene glycol. ANP-6-aminocaproyl, ANP-11-aminoundecanoyl, and ANP-polyethylene glycol are preferred. Aryl ketones preferred for use as photochemically reactive groups include benzoylbenzoyl and nitrobenzyolbenzoyl groups.

As will be noted from the foregoing description, the photoreactive groups are for the most part aromatic and hence generally are hydrophobic rather than hydrophilic in nature, the benefit of which will be explained below.

Reactive groups also include thermochemical groups (that are activated by heat energy), and are typified by and include nitrophenylhalides, and alkylamino, alkylcarboxyl, alkylthio, alkylaldehyde, alkylmethylimidate, alkylisocyanate, alkylisothiocyanate and alkylhalide groups. Other such groups include hydroxyl groups, primary amino groups, thio groups and maleimides. N-oxysuccinimide carboxylic esters of such groups as 6-amino hexanoic acid and amino undecanoic acid, alkylthio groups such as mercaptosuccinic anhydride and beta-mercaptopropionic acid, homocysteinethiolactones, and polyetheylene glycol derivatives are preferred. It will be noted from the foregoing description that many of the thermal chemical groups, such as carboxyl, hydroxyl and amine groups, are hydrophilic or water loving groups. The photochemical reactive groups and [some of the] thermochemical reactive groups are examples of latent reactive groups, that is groups that become reactive in response to a given external stimulus, and the use of latent reactive groups for the groups which covalently bond to the support surface and biomolecules, respectively, are preferred. Such groups are selected so that one of the groups responds to stimulus to which the other group does not respond.

The chemical chain backbones that are used as spacers in accordance with the invention may be made from a variety of chemical species, including naturally occurring and synthetic polymers, particularly including homopolymers and copolymers, protein chains and the like. The chemical chain forming the spacer backbone preferably has hydrophilic groups associated with it, such as ether groups, ketone groups and the like. Proteins may be polypeptides such as polylysine. Polysaccharide spacer chains such as chitosan, dextran, heparin, hyaluronic acid and various starches and celluloses may be employed.

Particularly preferred are spacers having backbone chains comprising repeating units that can be made from the polymerization of various monomers and oligomers. Particularly preferred are chains having repeating ethoxy ($-CH_2-CH_2-O-$) or isopropoxy ($-CH_2-CH(CH_3)-O-$) groups, and of these, poly(ethylene glycol) (PEG) is most preferred. Spacer chains formed of repeating units can generally be manufactured in varying lengths; this, in turn, permits a biomolecule to be spaced by varying distances from a supporting surface. In a specific and preferred embodiment, the method of the invention relates to a method for chemically tethering a biomolecule to a supporting surface so a to substantially optimize the activity of the biomolecule. The method comprises attaching a biomolecule to spacers of different lengths, the spacers being of a chemical species that ca be prepared in varying lengths without substantial change in chemical properties, the other ends of the spacers being joined by means of a covalent bond to a solid support. The varying extended spacer lengths spacing the biomolecule from the support surface each exceed 25 Angstroms and may vary up to and beyond several hundred Angstroms. The activity of the biomolecule is measured, and the spacer length that provides the biomolecule with an optimum or substantially optimum activity is chosen.

"Substantially optimum activity", as used herein, means activity that is at least about 50% as great as the optimum activity measured by the above method, the optimum activity being the greatest activity that is measured or being the activity at the point in which further increases in spacer length result in insignificant activity increases.

The spacers of the invention, as noted, have an extended length between reactive groups of at least 25 Angstroms and preferably at least 50 Angstroms. The reactive groups for attachment to a biomolecule and to a supporting surface may be positioned as desired along the length of a spacer chain, but preferably are carried as the end or terminal groups of the spacer chain.

The spacer chain itself desirably is solvophilic, e.g., the spacer chain is generally water loving and tends to uncoil in an aqueous environment. By far the majority of biomolecules are generally hydrophilic in that they are adapted for use in aqueous environments since, with few exceptions, body fluids are aqueous in nature. The spacer chemical chains, without end groups, desirably are at least partially soluble—to the extent of not less than about 0.5% by weight—in water at 25° C.; preferably, the solubility of the spacer chemical chains in water 25° C. is at least about 2% and, most preferably, the spacer chemical chains are water miscible. The presence on a spacer chain of a comparatively hydrophobic reactive group such as an aromatic photoreactive group, appears to have the unique effect of causing the spacer molecule to orient itself in an aqueous solution with respect to a hydrophobic support surface such that the comparatively hydrophobic reactive group is preferentially carried near the support surface while the remainder of the spacer molecule generally stands away from the hydrophobic surface; it is postulated that this feature enables spacers to be covalently bonded densely to a comparatively hydrophobic support surface, and this in turn contributes to the formation of a biocompatible "effective" surface as defined above.

A particularly preferred embodiment of the invention comprises a spacer backbone chain carrying at one end a photoreactive group and, at the other end, a biomolecule, the spacer having an extended length of at least about 25 Angstroms and preferably at least 50 Angstroms, measured along its extended length between the photoreactive group and the biomolecule. Particularly preferred, in this embodiment, are PEG spacers.

The loading density of biomolecules to a support surface can be increased by incorporating a guiding group in the spacer chain adjacent the latent reactive group that covalently bonds to a support surface. The guiding group may be monofunctional, being bound to the spacer chain or latent reactive group as a pendant group, or, preferably, is a difunctional group positioned desirably between the latent reactive group and the remainder of the spacer chain. The guiding group may be hydrophobic or hydrophilic as the case may be, and is chosen to be hydrophobic when the support surface is hydrophobic, and hydrophilic when the support surface is hydrophilic, all for the purpose of preferentially orienting the latent reactive group of the spacer in bonding proximity to the support surface. As pointed out above, the long chain spacers of the invention commonly are employed in the form of a solution that is applied to a support surface, the liquid vehicle of the solution affording the long chain spacer a degree of mobility. The guiding group hence also may be defined as a group that is hydrophobic when the spacer molecule is employed in a hydrophilic liquid medium, or hydrophilic when the spacer is employed in a hydrophobic liquid medium.

To restrain spacer chains from becoming deeply imbedded in a support surface, another group, herein termed a "stopping" group, may be included in the spacer chain. The stopping group is generally opposite in sense to the guiding group in terms of solvophilicity; and hydrophilicity; that is, the stopping group is chosen to be relatively hydrophilic when the support surface (and guiding grup, if used) is hydrophobic and is chosen to be relatively hydrophobic when the support surface (and guiding group, if used) are hydrophilic. Put another way, the stopping group is a group that is hydrophilic when the support surface is hydrophobic and hydrophobic when the surface is hydrophilic liquid medium is hydrophobic.

The "stopping" group is bifunctional and, when used, is always positioned such that the latent reactive group and the guiding group are nearer the support surface than is the stopping group. The stopping group is preferably positioned between the bulk of the long chain spacer and the guiding and latent reactive groups.

Spacer chains utilizing guiding and stopping groups hence may schematically be represented as:

(latent reactive group)—(guiding group)—(stopping group)—(spacer chain).

In a generally hydrophilic liquid system employed to bond biomolecules to a relatively hydrophobic surface, examples of guiding groups (hydrophobic groups, in this example), include groups derived from epsilon amino caproic acid ("EAC"), aminoundecanoic acid ("AUD") and other aminoalkyl carboxylic acids such as gamma aminobutyric acid and beta-alanine. Stopping groups (hydrophilic, in this example) include canine serum albumin ("CSA"), mono and polysaccharides, cysteic acid, gluconic acid, and other ionizable groups such as sulfonic acids of which taurine is an example.

"Hydrophilic" and "hydrophobic" are used herein to describe compositions broadly, as water loving and water hating, respectively, in line with the following observations: Hydrophilic compounds are usually relatively polar and often are ionizable. Such compounds usually bind water molecules strongly. Hydrophobic compounds are usually relatively non-polar and non-ionizing. Hydrophobic surfaces will generally cause water molecules to structure in an ice-like conformation at or near the surface. "Hydrophobic" and "hydrophilic" are relative terms, of course, and are used herein in the sense that various compositions, liquids and surfaces may be hydrophobic or hydrophilic relative to one another. A discourse on the subject is found in Hoffman, *Letter to the Editor: A general classification scheme for "hydrophilic" and "hydrophobic" biomaterial surfaces*, J. Biol. Mat. Res. 20, pp. ix-xi (1986).

The invention may be more easily appreciated by reference to the following, non limiting examples, in which parts are expressed by weight unless otherwise indicated.

EXAMPLE 1

This example describes one way in which the length of a spacer may be adjusted so as to provide optimum activity to an associated biomolecule. Diamino polyethylene glycol polymers (sold under the trade name Jeffamine, Jefferson Chemical Co.) were coupled directly to Pall membranes (Pall Biosupport Division) through free amine coupling of the polymers to the membranes. The diamino polyethylene glycol polymers were of molecular weights of 600, 900, 2000 and 3500 daltons, providing chain lengths of about 60, 90, 190 and 330 Angstroms, respectively. All non covalently linked spacers were washed from the membranes.

Figure 1:
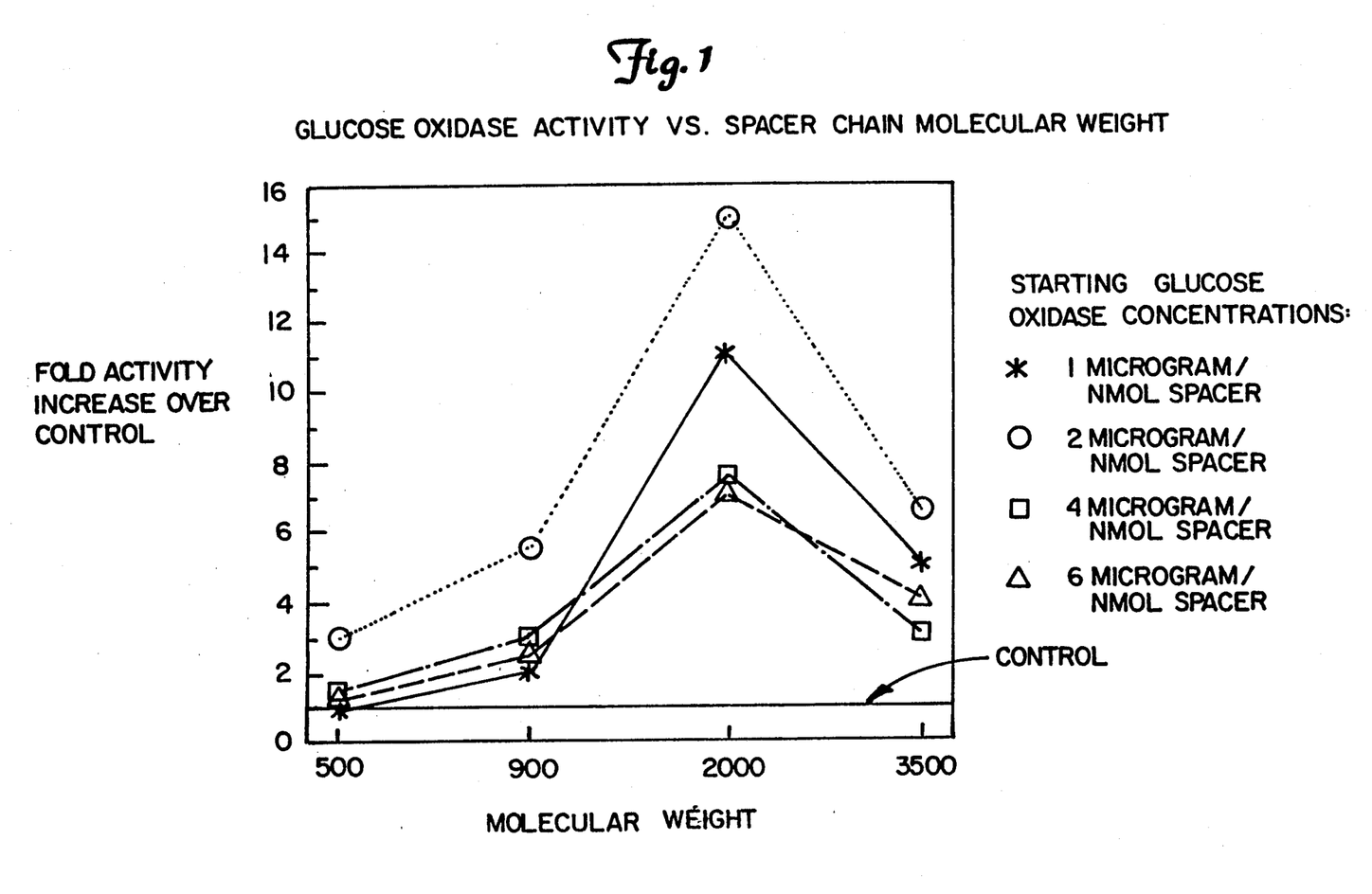
FIG. 1 is a graphic representation of biomolecule activity as a function of spacer chain molecular weight, as reported in Example 2 below.

Glucose oxidase was then added to the activated membranes by glutaraldeyde coupling to the remaining terminal amine of the spacer arm. The starting concentrations of enzyme were approximated to 1, 2, 4 and 6 nanograms of enzyme per nanomole of immobilized spacer arm. Tritiated glucose oxidase was used so that the total amounts of immobilized enzyme could be assayed by liquid scintillation techniques. Fixed point enzyme assays were performed on each starting concentration of enzyme. From these analyses, the specific activities of the immobilized enzyme were determined and normalized against controls comprising enzyme directly covalently bound to the membranes. The greatest increase in enzyme activity was found at a spacer molecular weight of 2000, corresponding to an extended chain length of about 190 Angstroms. The results of this experiment are graphically depicted in FIG. 1.

Following this experiment, the spacer chain comprising diamino PEG of molecular weight 2000 can be attached at one end to a photogroup such as ANP and at its other end to glucose oxidase. This product, in aqueous solution, may be covalently bonded to a suitable support surface by exposure to light and can be used in enzyme immunoassays.

EXAMPLE 2

This example describes the attachment, via a long chained polyethylene glycol spacer of molecular weight 2000 and having an extended length of about 190 Angstroms, of a biomolecule (urokinase) to a section of polyurethane tubing to reduce the thromogenic characteristics of the tubing surface. Initially, canine serum albumin (CSA) was bonded to the photoreactive group azidonitrophenyl-6-aminocaproyl-N-oxysuccinimide ("ANP-EAC-NOS"), the resulting material being photocoupled to polyurethane tubing through the ANP group. To the CSA group was then added the polyoxyethylene chain which in turn was provided with a urokinase end group.

200 milligrams of CSA (Canine Serum Albumin) were dissolved in 10 ml of 0.1M borate buffer, pH 9.0. Azidonitrophenyl-6-aminocaproyl-N-oxysuccinimide (ANP-EAC-NOS was dissolved in dimethylformamide at 20 milligrams/milliler, and 567 microliters of the ANP-EAC-NOS solution was added to the CSA solution at room temperature under darkroom conditions. After stirring constantly for 8 hours, the solution was dialyzed extensively at 4° C. Based on the absorbance at 460 nanometers, it was calculated that 8.64 ANP groups were coupled per CSA molecule.

Pieces of polyurethane tubing ("PUT"), having their ends plugged with small pieces of glass rod to prevent liquid from getting inside, were immersed in the above solution for 2 hours in the dark. These pieces were then removed and exposed to visible light for 1 hour. This procedure was repeated one more time for each piece. The PUT pieces were then immersed in the ANP-EAC-CSA solution overnight followed by a one hour exposure to visible light.

Thirty milligrams of polyoxyethylene bisamine (PEG-diamine, "Jeffamine ED 2001"from Texaco, of about 2000 molecular weight) were dissolved in 1 milliliter of water and the pH was adjusted to 4.0 with 1N HCl. Separately, 200 milligrams of 1-ethyl-3-(3-dimethyl- aminopropyl)-carbodiimide (EDC) were dissolved in 5 milliliters of water. The PUT samples were immersed in the EDC solution, then the PEG-diamine solution was added. The reaction was then allowed to proceed for two hours at room temperature, after which, another 200 milligrams of EDC was added and the reaction mixture was permitted to stand overnight.

The PUT pieces were reacted with 1.25% glutaraldehyde at pH 6.8 overnight at room temperature, rinsed, and immersed in a solution of urokinase (8.3 units/milliliter, about 2-3 milligrams/ milliliter) and allowed to react overnight at 4° C. The tubes were washed to remove uncoupled urokinase and were then assayed for urokinase activity by activation of plasminogen and digestion of azocasein. Measurements indicated that 0.188 micrograms of urokinase had become immobilized per piece of polyurothane tubing.

EXAMPLE 3

Endothelial Cell Attachment/Growth

Various cell factors were coupled to polymeric surfaces tested in vitro to determine the effect of these factors upon cell attachment and overgrowth. The polymeric surfaces included polyvinyl chloride (PVC), polyethylene (PE), polypropylene (PP) and polytetrafluoroethylene (PTFE) GORE-TEX (6 mm reinforced expanded PTFE, a trademarked product of W. L. Gore and Associates, Inc.). Commercial tubing tested included polyester (Dacron, D, 6 mm straight knitted dacron velour, a trademarked product of Dupont), silicone elastomer, (Silastic®, "S", 0.03-inch I.D., tubing, a trademarked product of Dow Corning) and polyurethane. Polystyrene plates were used as controls.

Chemical Linking Moieties. The chemical linking moieties used in these examples were the N-oxysuccinimide (NOS) esters of 4-azido-2-nitrophenyl epsilon amino caproic acid (ANP-EAC), 4-azido-2-nitro-phenyl amino undecanoic acid (ANP-AUDA) and benzoylbenzoic acid (BBA).

Covalent Binding of Collagen to Spacers. Collagen was diluted to 2.0 mg/ml in 0.1M MES, pH 5.0. ANP-PEG-NH$_2$ or BBA-PEG-NH$_2$ (molecular weight 1450) was added in a 10× molar excess over the collagen. Next, three 10 × molar excesses of EDC were added at half hour intervals. After four hours of stirring at room temperature, the product was dialyzed against PBS to remove non covalently bound photoreagents and PEG-NH$_2$ spacers. The product was analyzed by UV spectroscopy and protein assay to determine the photogroup:protein ratios. A ratio of 11 was commonly observed.

Covalent Binding of Biocompatible Agents to Plastic Surfaces. Various sheets, tubes and flat pieces of polyethylene, polyvinyl chloride, polypropylene, polyurethane, Dacron® (velour), Silastic® (medical grade), and polytetrafluroethylene above were used. A 0.05 ml aliquot of solutions containing 0 to 500 ug/ml of the photolabeled biocompatible agent prepared as above was added to each 0.5 cm$^2$ section of plastic surface. The solution was allowed to adsorb onto each piece for 3 hours at room temperature in the dark. The excess liquid was removed and the biocompatible agents were covalently linked to the surfaces by photolysis for 12 hours at the appropriate wavelength (Tungsten spotlite for ANP and long wavelength UV for BBA). After photolysis, the specimens were washed with a 4 second stream of PBS to remove non-covalently linked molecules of photolabeled biocompatible agent. The pieces were then placed in tissue culture to assess the endothelial cell reaction to the cell factors, reported below.

IN VITRO TESTS PERFORMED WITH MODIFIED SURFACES

A. Radio-labeled biocompatible agents

Radiolabeled [$^3$H] collagen was photolabeled as described above to provide ANP-EAC-PEG-Collagen, the latter being photocoupled to plastic surfaces. The plastics surfaces were extensively washed with PBS, then dissolved in organic solvent, and counted by liquid scintillation spectrometry. Some representative results are given in the Table 1, evidencing covalent coupling to the surfaces.

TABLE 1

| Solid Surface | Ng Growth Factor Applied/cm$^2$ | Ng Growth Factor Photocoupled/cm$^2$ | % Coupling Efficiency |
|---|---|---|---|
| PVC | 2680 | 374 | 14.0 |
| Polyurethane | 2680 | 2170 | 81.3 |

B. Attachment of Bovine Endothelial Cells to Modified Plastic Surfaces

Bovine endothelial cells were collected from fetal animals 8-24" in length. Cornea, aorta and umbilical endothelial cells were harvested aseptically. Cells were grown in a 5% CO$_2$ incubator at 37° C. in a known high glucose cell growth medium such as Dulbecco's modified Eagle's medium (described in R. Dulbecco and G. Freeman, *Virology*, Vol. 8:396 (1959) and J. D. Smith, G. Freeman, M. Vogt and R. Dulbecco, *Virology*, Vol. 12:185-196 (1960)) with 25 mmole HEPES buffer, 10% bovine calf serum, and 2.5 micrograms amphotericin B/ml (the "growth media"). Once the plates, tubes or sheets were prepared; cell cultures were prepared from primary cell lines. The cells were detached from the cell lines with a 0.25% solution of trypsin and resuspended in the growth media. Cells were then counted using a trypan blue (0.4%) solution and a hemocytometer. Various concentrations of cells were layered on the prepared materials. Cell attachment was monitored for various time periods from 5 minutes to 14 days. Attachments were determined by at least two methods. In one, sample materials were removed from culture media and washed 2 times with sterile saline. Cell stains were then applied and total cells on the surface were counted. A second method was to trypsinize the cells off the surface with a trypsin solution and count using the trypan blue method.

Representative results of the attachment and outgrowth of endothelial cells on precoated polyvinyl chloride plastic pieces are reported in Table 2. The number of viable cells attached to each piece were determined by trypan blue staining procedures.

TABLE 2

| Biocompatible agent and chemical-linking moiety | Ng growth factor/cm$^2$ | 3-day cell counts | 7-day cell counts | 7-day outgrowth |
|---|---|---|---|---|
| ANP-EAC-PEG-JEFF-COL | 374.0 | 14500 | 15800 | 1.0-3.0 mm |
| Control PVC | | 0 | 7 | 1.5-2.0 mm |

C. Attachment of Human Umbilical Endothelial Cells

Primary human endothelial cells were harvested from fresh (less than 4 days old) human umbilical cords. Cords were rinsed with 20 mls-cord buffer (0.144M NaCl, 0.004M KCl and 0.001M PO$_4$) twice to remove blood and clots. Collagenase was pushed into the cord and left for 20 minutes at room temperature. Using 10 ml of warm cord buffer, the collengenase and detached cells were flushed into tubes. The suspension in the tubes were combined and centrifuged at 1500 rpm for 5-10 minutes. The supernatant was poured off and the cells resuspended in 10 ml of cord buffer. Following the second centrifugation, the cells were resuspended in cord buffer and plated into tissue culture disks. All cells were incubated in 37° C. incubator with 5% CO$_2$. Cells were radiolabeled using $^{51}$Cr in cord media without calf serum.

Labeled cells were then used for cell attachment studies. Plates, sheets, and tubes of the plastics described above were prepared as recorded above. The cells were trypsinized and counted with the trypan blue method. Cells were allowed to adhere to the prepared plastic for three hours to seven days. Cells were rinsed off and the total number of attached cells were compared to the number of non-attached cells. Results comparable to those appearing in Table 3 above were obtained.

D. Outgrowth Measurement using Endothelial Cells

The following techniques were used to monitor the outgrowth of cells from a point of origin as the cells grow to cover the surfaces of the plastics listed above. Solutions of biocompatible agents comprising from 0 to 500 micrograms of cell factors were coated onto surfaces from 1 to 6 cm long to establish a gradient. Cells were not detached from the tissue with trypsin or any proteinase. The tissue was placed on a point of origin at the low end of the gradient and marked. The tissue was allowed to sit for 15 minutes at room temperature. Growth media was added to give a moist coating over the plastic. All protocols were carried out using aseptic conditions. Plates were then incubated at 37° C. in a 5% CO$_2$ incubator. Outgrowth was measured daily for up to two weeks or until the length of plastic was completely covered. Outgrowth on the treated surfaces was compared to nontreated control surfaces as reported in Table 2 above. All materials were rinsed and stained for permanent scanning electron microscopy.

These results demonstrated that the covalent attachment of the growth factors fibronectin (FN) and collagen (COL) to the plastic surface improved the biocompatibility of the plastic with bovine endothelial cells. The cells preferentially attached to the modified surfaces versus control surfaces, as indicated by the distance they grew out over the plastic surface.

EXAMPLE 4

Modification of the Surfaces of Contact Lenses and Introcular Lens Implants

The experiments described in this example involved measuring the in vitro protein deposition from artificial tear solutions onto prepared lenses in comparison to non-treated lenses.

BINDING BIOCOMPATIBLE AGENTS TO THE CHEMICAL LINKING MOIETY

A. preparation of Photolabeled Polyethylene Glycols

Polyethylene glycols of molecular weights 1000 (PEG-1000) and 4000 (PEG-4000) were labeled with fluoronitroazidobenzene (FNAB) by modification of the phase transfer method of Kimura, and S. Regen, Journal of Organic Chemistry 48; 195 (1983), the teachings of which are incorporated by reference herein. Briefly, the phase-transfer synthesis of 4-azido-2-nitrophenyl polyethylene glycol (ANP-PEG) involved the mixture of 60% aqueous potassium hydroxide toluene with FNAB and PEG, followed by extraction and thin layer chromatographic (TLC) purification as described below.

ANP-PEG-1000. ANP-PEG-1000 was prepared by adding 0.05 mmole PEG-1000 to 5 mls 60% KOH and 0.5 mmole FNAB to 10 ml toluene. This reaction mixture was rapidly stirred at room temperature for 16 hours. The product was isolated from the organic solvent layer. This layer chromatography ("TLC") in 85/15/1/1/ chloroform/methanol/$H_2O$/ acetic acid or ammonium hydroxide separated mono- and di- substituted derivatives of ANP-PEG-1000 from unlabeled PEG. The band corresponding to ANP-PEG-1000 (lower $R_f$ value) was extracted from silica gel with TLC solvent and azeotrophed to remove residual acid or base. The final product was soluble in water and resulted in the conversion of 30-40% of the PEG starting material to ANP-PEG-OH product.

ANP-PEG-4000. The ANP-PEG-4000 was prepared by the same procedure as that described above except that the reaction mixture was rapidly stirred at 50° C. to ensure all reagents remained in solution during the course of the reaction. The yield of ANP-PEG-4000-OH was 10%.

B. Preparation of Photolabeled Spacers

Polyoxypropylenepolyamines and polyoxethylenepolyamines (referred to as "Jeffamines", a trademark of Jefferson Chemical Co., Inc.) were photolabeled by coupling the N-oxysuccinimide ("NOS") esters of ANP-EACA, BBA and nBBA to the polymers. These NOS-derivatives were added in 0.5× amounts to 1× Jeffamine in very dry (high purity) solvents (ANP-EAC-NOS in dry tetrahydrofuran, BBA-NOS in dry dioxane or dimethylformamide and nitro BBA-NOS in dry dioxane or dimethylformamide). After 16 hours of reaction at room temperature in the dark, the products were isolated by TLC in 85/15/1/1/ chloroform/methanol/$H_2O$/acetic acid. Monosubstituted Jeffamine derivatives were extracted with the TLC solvent and azeotrophed with water to remove the residual acetic acid. The water-soluble products ANP-EAC-Jeffamine, BBA-Jeffamine, and nBBA-Jeffamine were isolated in 15%, 10% and 12% yields, respectively.

C. Preparation of ANP-Hyaluronic Acid

The terminal sugar of human placental hyaluronic acid ($MW_{app}$100,000-130,000) was activated by the periodate procedure described in E. Junowicz and S. E. Charm, "The Derivatization of Oxidized Polysaccarides for Protein Immobilization and Affinity Chromatography," *Biochimica et Biophysica Acta*, Vol. 428: 157-165 (1976), incorporated herein by reference. This procedure entailed adding sodium or potassium periodate to a solution of hyaluranic acid thus activating the terminal sugar. The hyaluronic acid was added to a 10-fold excess of Jeffamine and allowed to react 4 hours at room temperature. The linkages were stabilized by reduction with sodium cyanoborohydride, followed by exhaustive dialysis to remove most of the excess Jeffamine. A 10-fold molar excess of ANP-EAC-NOS in DMF was added to the Jeffamine-hyaluronate in 0.1M carbonate, pH 9.0, by syringe drive. This addition required 16 hours and was conducted at room temperature in the dark. The excess ANP-EAC-NOS and ANP-EAC-Jeffamine was removed by gel filtration chromatography. The integrity of the azide group, required for photocoupling of the moiety to the contact lens polymer backbone, was analyzed by infrared spectroscopy to detect the ANP group, a polyethylene glycol assay to detect the Jeffamine spacer, and a modified carbazole assay described in T. Bitter and H. Muir, *Analytical Biochemistry* Vol. 4: 330-334 (1962) to determine the uronic acid content of the derivative.

The fractions containing one ANP, one Jeffamine and one hyaluronate molecule were pooled and used as a biocompatible agent.

D. Preparation of Photolabeled Hyaluronic Acid, Methyl Cellulose and Chondroitin Sulfate ANP-EAC-Jeffamine, BBA-Jeffamine and nitro-BBA-Jeffamine were linked to the carboxyl groups of uronic acid residues of hyaluronic acid and chondroitin sulfate by a carbodiimide procedure as follows. A 5 molar excess of photolabeled Jeffamine and 1-ethyl-3-(3-dimethylaminopropyl) carbodiimide with HCl was mixed with the polysaccharide polymer in water adjusted to pH 4.5 with 0.1N HCl. The mixture was allowed to react at room temperature in the dark for 24 hours. The product was purified by gel filtration chromatography then analyzed for photogroup and carbohydrate content as described above.

2. Photocoupling Biocompatible Agents to Lens Surfaces

The photolabeled biocompatibles agents obtained above were added to contact lens materials at a concentration of 250-1000 pmole agent/contact lens. The solution was allowed to adsorb onto the contact lenses at room temperature in the dark for 3 hours. The photolabeled agents were then covalently linked to the plastic by photolysis for 12 hours at the appropriate wave length (450 nm for ANP and 320 nm for BBA and nBBA derivatives). After photolysis, the contact lenses were washed with 5×5 ml of normal saline (0.85% NaCl) to remove non-covalently linked groups.

3. In Vitro Protein Adsorption Studies. Artificial human tears were prepared according to the formula found in B. P. Gloor, "The Lacrimal Apparatus" in *Adler's Physiology of the Eye: Clinical Applications* (R. A. Moses, ed.), C. V. Mosby Co., St. Louis, Mo. (1981) the teachings of which are incorporated herein. As indicated in that reference the major proteins present in human tears are serum albumin (HSA), gamma-globulin (HGG), and lysozyme (LYZ). The major sterols present in human tears are cholesterol and cholesterol esters.

Preparation of Artificial Tears. The radiolabeled proteins described above were used in preparation of artificial tears. One of the radiolabeled proteins or tritiated cholesterol wa included in each tear mixture. The other components were not radiolabeled. The contact lens materials were incubated in the artificial tear solution for one week at 37° C. with gentle agitation. At the end of this time the lens materials were washed with 5×10ml of 0.85% NaCl. The amount of protein adsorbed to the lens materials was then determined by liquid scintillation counting.

In vitro protein deposition results indicated significant decreases in protein deposition from artificial tears on certain of the contact lens materials during a one week period.

EXAMPLE 6

Coupling of Films to Solid Surfaces

Photolabeled derivatives of hyaluronic acid (ANP-EAC-Jeffamine, BBA-Jeffamine and nitro-BBA-Jeffamine) are prepared. Films are formed from the photoreactive coating material and placed on surfaces of contact lenses (by dipping and drying) in the dark. Covalent attachment to the biomaterial surface and strengthening of the film by intermolecular cross-linking may be accomplished through illumination.

In another example, an artificial hip joint is soaked in ANP-EAC-Jeffamine-hyaluronic acid (0.1:1 mg/ml) for three hours in the dark. The joint is then removed from solution and allowed to dry forming a thin film of coating material on the artificial joint. The film is then covalently attached to the joint by illumination at 400 to 450 nm for 8 hrs. at 4° C. The joint is then rinsed in physiological saline to remove uncoupled ANP-EAC-Jeffamine-hyaluronate. The hyaluronic acid bound to the bone reduces friction and reduces wearing of the bone in the joint area.

EXAMPLE 7

This experiment describes the covalent attachment of biomolecules to commercial Interocular Lens (IOL) materials to improve the long term biocompatibility of the IOL with the eye.

Synthesis of Photoreagents

Azido-Nitrophenyl-groups. The fluro-nitro-azido benzene ("FNAB") coupling group was prepared from 4-fluoro-3-nitro aniline. The aniline (10.0 g) was added to 60 ml MCl and 10 ml $H_2O$. The mixture was warmed to 40°–45° C. with stirring. A 5.60 g portion of $NaNO_2$ was dissolved in 9.0 ml $H_2O$ and 5.60 g $NaN_3$ was dissolved in 15.0 m. $H_2O$. The aniline/HCl mixture was cooled to −20° C. in a dry ice/isopropanol bath, followed by drop-wise addition of the $NaNO_2$ solution over 15 minutes. After completion of the addition, the mixture was stirred an additional 15 minutes at −20° C. The $NaNO_3$ solution was added drop-wise over 30 minutes, while the reaction mixture was maintained at 20° C. to −10° C. A small amount of ether was added to reduce foaming. After 30 minutes of stirring at −20° C., ice cold $H_2O$ was added to precipitate the product, then the FNAB was collected by filtration. After drying the product was crystallized from 30°–60° C. petroleum ether. A 72.6% yield of product resulted from this procedure.

4-Azido-3,5-Dichloro-2,6-Difluoro-Pyridinium group. A 1.010 g (5.0 mmole) portion of 3,5-dichloro 2,4,6-trifluoropyridine was weighed into a 50-ml round bottomed flask and diluted with 20 ml of acetonitrile. The 5.0 mmole (325 mg) of $NaN_3$ was added in 10–15 mg portions at room temperature and the reaction was monitored for exothermic reaction. The solid azide appeared to have limited solubility in the acetonitrile. The reaction was allowed to run for a total of two hours. Thin layer chromatography ("TLC") in a petroleum ether solvent system indicated that all of the starting material had been reacted. The acetonitrile was removed under reduced pressure on a cool water bath, resulting in the formation of an oily solid. The product was dissolved in 40 ml ether and 10 ml $H_2O$, shaken in a separatory funnel, and the aqueous layer was removed. The ether layer was washed with $H_2O$ and the combined water washes were back extracted with 10 ml ether. The combined organic fractions were dried over $MgSO_4$. The TLC demonstrated the formation of product. A 95.7% weight yield of crude product in the form of a clear oil was obtained.

Synthesis of Photolabeled Surface Modification Reagents. The structures of the photolabeled surface modification reagents are given in Table 4. The derivatives of the polyethylene glycols ("PEG") were prepared by methods referred to in the previous examples. The 4-Azido-3,5-Dichloro-2,6-Difluoro-Pyridine derivative of the PEG's was accomplished by addition of this group to bis-amino-PEG's, followed by purification by thin layer chromatogrophy on an 85:15:1:1 chloroform:methanol:$H_2O$:acetic acid system.

The photoactivatable derivatives of hyaluronic acid and chondroitin sulfate were prepared by addition of ANP-PEG-$NH_2$, BBA-PEG-$NH_2$ or N-(4-Azido 3,5-Dichloro-6-Fluoro-Pyridinyl)-PEG-$NH_2$ to a solution of the hyaluronic acid substance in the presence of water soluble carbodiimide 1-ethyl-3-(3-dimethylamino-propyl) carbodiimide (EDC). The resulting derivatives were purified by gel filtration chromatography on a Bio-Rad P-200 column or by dialysis and were examined by uronic acid analysis polyethylene glycol assay, spectrophotometric analysis to determine the presence of the photogroup and by infra-red spectroscopy to assess the integrity of the azido or carbonyl functions of the photogroups. Further explanations of the synthesis and characterization of these agents are described below.

Procedure for Coupling Photogroups to Collagen. Collagen was diluted to 2.0 mg/ml in 0.1M MES, pH 5.0. ANP-PEG-$NH_2$ (molecular weight 1450) was added in a 10× molar excess over the collagen. Next, three 10× molar excesses of EDC were added at half hour intervals. After four hours of stirring at room temperature, the product was dialyzed against PBS to remove non covalently bound photoreagents and PEG-$NH_2$ spacers. The product was analyzed by UV spectroscopy and protein assay to determine the photogroup:protein ratios. A ratio of 11 was commonly observed.

Preparation of ANP-PEG-$NH_2$, BBA-PEG-$NH_2$ and ADDP-PEG-$NH_2$. The Bis-amino poly(oxyethylene)-glycol and poly(oxypropylene) glycol polymers were labeled with the photoactivatable coupling reagents in a manner similar to that described for proteins, but both the polymers and the photogroups were soluble in organic solvent. A 0.5× molar ratio of photogrou to PEG was added to the synthetic polymer in dry solvent (dioxane, dimethyl formamide or tetrahydrofuran) and left to stir at room temperature in the dark for 16 hours. At the end of that time, the mono-labeled PEG product was purified from the starting materials by thin layer chromatography in an 85:15:1:1 chloroform:methanol:H₂O:acetic acid system.

Preparation of ANP-PEG-1450. The ANP-PEG was prepared in general by the Phase Transfer reaction previously referred to. Fluoro-nitro-azido benzene and the PEG were dissolved in toluene, followed by the addition of KOH to give a final concentration of 60%. The mixture was stirred to insure emulsion formation and heated at 35°-40° C. for a total of 18 hours. The reaction was monitored by TLC using a 9:1 $CH_2Cl_2$:methanol solvent system. The di-ANP and mono-AMP products were visualized under UV light and all three products gave an orange coloration with Dragendorff's reagent. A selective extraction procedure was established for the mixture based on carefully increasing the ionic strength of the aqueous layer to force the PEG products into the toluene based on their relative polarities. After cooling the reaction mixture, the KOH layer was removed. Careful additions of saturated NaCl were made and the resulting toluene layers were monitored by TLC to assess the distribution of the free PEG, mono-ANP-PEG and di-ANP-PEG products. After all of the di-product had been removed, solid NaCl was added to the aqueous layer, and the mono-ANP product was extracted from the mixture with toluene. The extractions were repeated until TLC showed no more mono-ANP in the toluene layer. These extracts were combined, dried over $MgSO_4$ and evaporated under reduced pressure to give the desired mono-ANP-PEG product.

Preparation of Hyaluronic Acid and Chondroitin Sulfate derivatized with Photoactivatable Coupling Reagents. The terminal amino groups of ANP-EAC-PEG-$NH_2$ or BBA-PEG-$NH_2$ were coupled to the carboxyl groups of the hyaluronic acid or chondroitin sulfate using 1-ethyl-3-(3-dimethylamino-propyl) carbodiimide (EDC). The hyaluronic acid was dissolved in 0.1 MES buffer, pH 5.0. An amount of ANP-EAC-PEG-$NH_2$ or BBA-PEG-$NH_2$ equal to a 5× molar excess over the carbohydrate was added. Next, solid EDC was added at 5.0× molar ratios over the polysaccharide in three allotments over the course of one hour. After 6–8 hours of stirring, the products were purified by dialysis. The products were analyzed by UV spectroscopy, uronic acid assay and PEG assay to determine the photogroup:spacer:polysaccharide ratios. A typical ratio of 10 phorogroups to one hyaluronic acid and 9 photogroups to each chondroitin sulfate molecule was obtained.

Some compounds referred to herein are depicted in the following Tables 3 and 4.

TABLE 3

| Compound | Structure |
| --- | --- |
| Fluoronitroazidobenzene (FNAB) | $N_3$—⟨benzene⟩—F with $NO_2$ |
| Azido-nitrophenyl-epsilon amino caproic N-oxysuccinimide (ANP-EAC-NDS) | $N_3$—⟨benzene($NO_2$)⟩—NH—$(CH_2)_5$—C(=O)—O—N(succinimide) |
| Benzoyl benzoic acid (BBA) | ⟨Ph⟩—C(=O)—⟨Ph⟩—C(=O)—OH |
| Benzoyl benzoic N-oxysuccinimide (BBA-NOS) | ⟨Ph⟩—C(=O)—⟨Ph⟩—C(=O)—O—N(succinimide) |
| 4-Azido-3,5-Dichloro-2,6-Difluoro-Pyridine (ADDP) | $N_3$—⟨pyridine⟩ with Cl, F, Cl, F substituents |

TABLE 4

| Compound | Structure |
|---|---|
| Azido-nitro-phenyl-polyethylene glycol (ANP-GEG-1450) | $N_3$—(phenyl with $NO_2$)—$(OCH_2CH_2)_n$—OH |
| Benzoylbenzoic-polyethylene glycol (BBA-PEG-1450) | (phenyl)—C(=O)—(phenyl)—C(=O)—NH—$CH_2CH_2$—$(OCH_2CH_2)_n$—OH |
| Azido-nitro-phenyl-epsilon-amino-caproic-polyethylene glycol amine (ANP-PEG-$NH_2$) | $N_3$—(phenyl with $NO_2$)—NH—$(CH_2)_3$—C(=O)—NH—$CH_2CH_2$—$(OCH_2CH_2)_n$—$NH_2$ |
| Benzoyl-benzoic polyethylene glycol-amine (BBA-PEG-$NH_2$) | (phenyl)—C(=O)—(phenyl)—C(=O)—NH—$CH_2CH_2$—$(OCH_2CH_2)_n$—$NH_2$ |
| 4-Azido-3,5-dichloro-2-fluoro-amino polyethylene glycol amine (ADOP-PEG-$NH_2$) | $N_3$—(pyridine with Cl, F, Cl)—NH—$CHCH_2$($CH_3$)—$(OCHCH_2(CH_3))_a$—$(OCH_2CH_2)_b$—$(OCH_2CH(CH_3))_c$—$NH_2$ |
| Azido-nitro-phenyl-epsilon-amino-caproic polyethylene glycol hualuronic acid (ANP-PEG-HYAL) | PEG—ANP attached via CO to hyaluronic acid disaccharide repeat $[...]_n$ |
| Benzoyl benzoic polyethylene glycol hyaluronic acid (BBA-PEG-HYAL) | PEG—BBA attached via CO to hyaluronic acid disaccharide repeat $[...]_n$ |
| Azido-nitro-phenyl-epsilon-amino-caproic-polyethylene glycol chondroitin sulfate (ANP-PEG-CHON) | PEG—ANP attached via CO to chondroitin sulfate disaccharide repeat $[...]_n$ |

Attachment of Biomolecules to IOL Materials. IOL materials (PMMA buttons, polypropylene, polyethylene, silicone, dimethyl-siloxane, and PMMA lenses with polypropylene haptics) were immersed in a solution of the coating which had been dissolved in $H_2O$. After three hours of submersion, the lens materials were removed and quickly dried under a stream of air or nitrogen. The surface modification reagents were then covalently attached by photolysis at the appropriate wavelength. The lens pieces were then washed with deionized H₂O. To determine whether this coating procedure affected the surfaces of the lenses, scanning electron microscopy (SEM) was performed to evaluate the polish and finishes on coated versus control lenses.

The loading densities of the biomolecules were assessed using radiolabeled derivatives of the synthetic polymers and naturally derived biomolecules. Each matrix piece was analyzed by liquid scintillation spectrometry to determine the maximum number of micrograms of surface modification reagent for each square centimeter of matrix material. The efficiencies of counting were determined by standard additions of tritium labeled compounds to each of these matrices so that accurate assessments of loads could be made.

The results showed the covalent attachment of the photolabeled synthetic polymers, proteins and long chain polysaccharides substances to polyvinylchloride (PVC), polypropylene (PP), polyethylene (PE), silicone and polymethylmethacrylate (PMMA). Table 5 below illustrates the coupling efficiency to the various materials.

TABLE 5

| Modification Solution | Matrix[1] | ng Applied $cm^2$ | ng Bound $cm^2$ | % Coupled |
|---|---|---|---|---|
| ANP-PEG-Collagen | PVC | 788.26 + 13.53 | 271.32 + 10.70 | 34.42% |
| | PP | 788.26 + 13.53 | 167.08 + 18.28 | 21.19% |
| | PE | 788.26 + 13.53 | 144.78 + 17.68 | 18.37% |
| | Sil/Dow | 788.26 + 13.53 | 121.64 + 16.16 | 15.43% |
| | Sil/Dow | 43.92 + 3.85 | 37.22 + 8.34 | 84.74% |
| | Sil/Ref | 788.26 + 13.53 | 136.40 + 39.86 | 17.30% |
| | Sil/Ref | 43.92 + 3.85 | 20.92 + 5.78 | 47.63% |
| | PMMA | 1392.68 + 23.90 | 180.49 + 29.75 | 12.96% |
| | PMMA | 77.59 + 6.80 | 24.26 + 4.33 | 31.27% |
| ANP-PEG-HYAL[2] | PVC | 892.20 + 122.38 | 394.84 + 52.74 | 44.25% |
| | PP | 892.20 + 122.38 | 221.14 + 24.86 | 24.78% |
| | PE | 892.20 + 122.38 | 283.56 + 14.78 | 31.78% |
| | Sil/Dow | 892.20 + 122.38 | 401.23 + 92.03 | 44.97% |
| | Sil/Ref | 892.20 + 122.38 | 507.87 + 115.44 | 31.84% |

[1]Matrix pieces were of 0.5 cm² areas, except the PMMA pieces which were 0.283 cm²
[2]HYAL = Hyaluronic acid Wettability Measurements. Wettability measurements of coated versus uncoated IOL's of commercial PMMA or silicone films were made substantially as shown in "Protocol for Contact Angle Measurements at the Polymer-Water Interface", Appendix 7 of *Guidelines for Blood-Material Interactions: Report of the National Heart, Lung, and Blood Institute Working Group*, U.S. Department of Health and Human Services, page A-30, September, 1985. There was statistically significant improvement of the wettabilities of both PMMA and silicone materials when surface modified. This was indicated by lower contact angle measurements on surface-modified lenses as compared to control lenses, as illustrated in Table 6 below. There is significant improvement of wettability with the coatings on both materials.

TABLE 6

| Lens Material | Coating | Mean Contact Angle |
|---|---|---|
| PMMA | Uncoated Control | 80.45 + 2.39 |
| | ANP-PEG-NH₂ | 67.20 + 6.70 |
| | BBA-PEG HYAL | 74.65 + 3.93 |
| Silicone | None | 102.3 + 2.75 |
| | ANP PEG-NH₂ | 93.50 + 2.87 |
| | BBA-PEG-NH₂ | 90.40 + 4.10 |
| | ANP-PEG-HYAL | 66.50 + 5.37 |

[1]Mean contact angles are based on measurements of 10 left angles and 10 right angles for each coating and control.

Protein Adsorption Studies. The adsorption of proteins to the surface-modified versus control IOL materials was measured.

Tritiated type IV collagen, human serum albumin and human plasma fibronectin was prepared and diluted in Tear Electrolyte Solution. Gloor, B. P., "The Lacrimal Apparatus", in *Alder's Physiology of the Eye: Clinical Applications*, (R. A. Moses, ed.), C. V. Mosby Co., St. Louis, Mo. (1981). The modified and control PMMA lenses were then added to these solutions and allowed to adsorb proteins for seven days. At the end of that time, each lens was washed with buffered saline, dissolved in tetrahydrofuran, and analyzed by liquid scintillation spectrometry. The amounts of protein adsorbed to control PMMA lenses was compared to the amount adsorbed to surface modified PMMA lenses, and the results are given in Table 7 below.

TABLE 7

| Surface-Modification Reagent | Protein | Mean Microgram Protein/Lens[1] | Mean Reduction in Protein Adsorption |
|---|---|---|---|
| Control | Collagen | 0.76 + .02 | |
| ANP-PEG-HYAL | Collagen | 0.53 + .05 | 30.26 |
| Control | Fibronectin | 0.18 + .003 | |
| ANP-PEG-HYAL | Fibronectin | 0.14 + .005 | 22.22 |
| Control | HSA | 0.15 + .006 | |
| ANP-PEG-HYAL | HSA | 0.10 + .011 | 33.33 |

[1]The values for mean microgram protein/lens are the results of four replicates.

Biocompatibility Measurements Using Bovine Fetal Corneal Endothelial Cells. Pieces of Dow/Corning silicone, polypropylene, polyethylene, polyvinyl chloride and PMMA lens optics were treated with various surface modification reagents, photolyzed, and washed extensively with physiological saline. Two mm diameter buttons of cornea were collected from fetal animals 8-24 inches in length. The corneal pieces were greown in a 5% $CO_2$ incubator in Dulbecco's modified Eagle medium [69,70] with 25 mmole HEPES buffer, 10% fetal bovine serum, and 2.5 micrograms amphotericin B/ml at 37° C. The piece of cornea was then placed on one end of the rectangular pieces of IOL matrix materials, or in the center of the PMMA lenses. Cell attachment was monitored for seven days. The outgrowth of cells across the pieces was determined by measurement in mm, and the viabilities of the cells were determined by staining with a Wright-Geimsa stain or trypan blue stain. In order to avoid clouding of the IOL's, one would want to retard the adhesion of the corneal endothelial and epithelial cells to the IOL's, but not have a toxic or damaging effect on the cells. Further studies indicated that the surface modification reagents are non cytotoxic. Results are give in Table 8.

TABLE 8

In Vitro Biocompatibility Assessments of IOL's by Contact with Bovine Fetal Corneal Tissues

| Matrix | Modification Reagent | Mean Outgrowth | Viability Rating |
|---|---|---|---|
| PMMA | None | --------- | +3 |
| | ANP-PEG-Collagen | --------- | +3-+4 |
| | BBA-PEG-HYAL | --------- | +3-+4 |
| | ANP-PEG-HYAL | --------- | +3-+4 |
| Silicone | None | 0.00-0.10 mm | +1-+2 |
| | ANP-PEG-Collagen | 3.20 mm | +3-+4 |
| | ANP-PEG-HYAL | 0.47 mm | +3 |
| | BBA-PEG-HYAL | 0.67 mm | +3 |
| Polypropylene | None | 1.44 mm | +2-+3 |
| | ANP-PEG-Collagen | 5.00 mm | +3-+4 |
| | ANP-PEG-HYAL | 0.71 mm | +3 |
| | BBA-PEG-HYAL | 0.55 mm | +2-+3 |

[1] Viability ratings were based on a scale of +1 being no growth or just cell debris and +4 being fully viable, compact growth of cells.

G. Rabbit Cadaver Eye Assessment of Corneal Endothelial Damage

An abrasion test was conducted to determine whether the coatings might reduce the amount of endothelial damage caused by contact with the IOL. Fresh cadaver adult rabbit eyes were obtained within one-two hours after sacrifice. A 7-mm trephine was used to punch out a central corneal button which was placed on a microscope slide endothelial side up. A dry IOL was then picked up by a haptic and gently placed on the corneal button. Using very gentle taps (not pulling on the haptics), the lens was pushed across the corneal buttom twice at 90 degree angles from each other. The lens was then removed from the button by carefully grasping the haptic and gently sliding it off the button in a diagonal direction. The endothelium was then stained with 2-3 drops of a 25% stock solution of trypan blue for 1.5 minutes, rinsed, then stained with 2-3 drops of alizarin red (which was titrated to a pH of 4.2 with a solution of 0.1% $NH_4OH$ in 9.9% NaCl) for 3.5 minutes. Each lens was tested on 10 corneal buttons and the percentage of endothelial damage was estimated by reference to photographs showing varying degrees of endothelial damage. The treated lenses caused significantly less damage. The results of these studies are presented in Table 9 below.

TABLE 9

| Surface Modification Reagent | % Endothelial Cell Damage | Standard Deviation |
|---|---|---|
| Control Corneas | 1.57% | +0.73% |
| None | 22.75% | +5.41% |
| None | 18.30% | +6.89% |
| None | 25.75% | +4.62% |
| ANP-PEG-HYAL | 14.75% | +4.80% |
| ANP-PEG-HYAL | 13.25% | +5.60% |
| BBA-PEG-HYAL | 17.00% | +6.40% |
| BBA-PEG-HYAL | 13.00% | +4.30% |

I. Evaluation of the Biocompatibility of the Surface-Modified IOL's in the Cat Model Preoperative Evaluation. Ten healthy, unconditioned female cats ages 1.5 to 2.5 year of age were obtained from a commercial breeding colony. On the day of surgery, maximal pupil dilation was achieved with topical 10% phenylepherine drops. An extracapsular cataract extraction was performed using phakofragmentation and irrigation/aspiration. Lenses were individually numbered so that each cat received a control lens in one eye and a surface-modified IOL in the other. The surgeon did not know which lenses were coated and which were uncoated. Intraocular lenses were placed in the bag or the posterior sulcus. Once the lens was in position, the corneal section was closed with 8-0 nylon sutures. All animals under study were evaluated at 24 hours, 48 hours, one week and two weeks, Postoperative evaluation consisted of biomicroscopic evaluation for evidence of inflammatory damage as well as corneal endothelial cell studies. All animals were graded for inflammation. After animals were observed for the two week postoperative period, they were sacrificed and the eyes were taken for histological study. The eyes were fixed in Zenkers-Acetic acid and washed and stored in 70% alcohol.

Results of the Cat Model. The cat model was used as an implantation system for preliminary assessment of the acceptance of surface-modified IOL's by a host system. The results of the McDonald-Shadduck (inflammation) scores and pachometric readings are given in Table 10 below. As was anticipated, there was a low grade uveitis in all animals under study resulting in transient inflammation and corneal edema which did not fully subside during the two week healing period. However, the animals in the study did not present evidence of abnormal response to the lenses based on either in vivo or histological study. It was concluded that significant ocular abnormalities are not associated with coated intraocular lenses and that the endothelial cells of the cornea are protected by the coating process.

TABLE 10

In Vivo Biocompatibility Assessments of Surface-Modified IOL's in the Cat Model

| Cat # | Coating | Mean McDonald-Shadduck Score | | | | | Pachometric Readings | | | | |
|---|---|---|---|---|---|---|---|---|---|---|---|
| | | 0 hr | 24 hr | 48 hr | 7 day | 14 day | 0 hr | 24 hr | 48 hr | 7 day | 14 day |
| | None | 0 | 1.75 | 1.375 | 0.50 | 0.375 | 571 | 857 | 802 | 783 | 722 |
| | ANP-PEG HYAL | 0 | 1.75 | 1.25 | 0.50 | 0.350 | 572 | 714 | 776 | 695 | 649 |
| #2 | None | 0 | 1.875 | 1.875 | 0.50 | 0.375 | 586 | 933 | 796 | 753 | 673 |
| | ANP-PEG-HYAL | 0 | 1.625 | 1.250 | 0.50 | 0.375 | 605 | 686 | 654 | 679 | 645 |
| #3 | None | 0 | 1.50 | 1.50 | 0.50 | 0.375 | 648 | 868 | 924 | 833 | 832 |
| | ANP-PEG-HYAL | 0 | 1.50 | 1.50 | 0.50 | 0.375 | 625 | 860 | 884 | 831 | 791 |

TABLE 10-continued

In Vivo Biocompatibility Assessments of Surface-Modified IOL's in the Cat Model

| Cat # | Coating | Mean McDonald-Shadduck Score | | | | | Pachometric Readings | | | | |
|---|---|---|---|---|---|---|---|---|---|---|---|
| | | 0 hr | 24 hr | 48 hr | 7 day | 14 day | 0 hr | 24 hr | 48 hr | 7 day | 14 day |
| #4 | None | 0 | 0.875 | 0.875 | 0.375 | 0.350 | 537 | 825 | 691 | 679 | 650 |
| | ANP-PEG-HYAL | 0 | 0.875 | 0.875 | 0.375 | 0.250 | 549 | 757 | 660 | 663 | 561 |
| #5 | None | 0 | 0.750 | 0.500 | 0.375 | 0.250 | 584 | 622 | 685 | 706 | 830 |
| | ANP-PEG-Coll | 0 | 0.750 | 0.500 | 0.375 | 0.250 | 592 | 624 | 609 | 678 | 813 |
| #6 | None | 0 | 1.125 | 0.750 | 0.875 | 0.375 | 569 | 796 | 659 | 892 | 663 |
| | ANP-PEG-Coll | 0 | 1.125 | 0.750 | 0.875 | 0.375 | 582 | 736 | 728 | 706 | 653 |

The results of three cats were left out of this table because they developed severe respiratory infections during the course of this study which made accurate readings impossible.

EXAMPLE 8

This experiment describes the attachment of several antibodies to various support surfaces through the use of long chained hydrophilic spacers. Photoactive groups were employed to attach the spacers to the support surfaces, the photoactive groups comprising 4-fluoro-3-nitroaniline, benzoyl benzoic acid and 3,5-dichloro- 2,4,6-trifluoropyridine, all commercially available from Aldrich Chemical Company. The hydrophilic spacers were also procured from commercial sources. Bovine serum albumin (BSA), ribonuclease A (RN) and chicken egg white ovomucoid (OVO) were obtained from Sigma Chemical Corp. Diamino-polyethylene glycols were obtained from Texaco Chemical Corp. under the trademark Jeffamines ("JEFF"). Polyethylene glycol (MW 1450) was obtained from Sigma Chemical Corp. The support materials included Sephadex gels from Pharmacia), polystyrene beads, and polyvinyl chloride and polystyrene microtiter plates.

Coupling Photogroups to Protein Spacers. The proteins were diluted to 1.0-2.0 mg/ml in 0.1M sodium carbonate, pH 9.0. A 100× excess of the photogroup-NOS was added very slowly to the protein solution at a 4 mg/ml dilution in dimethyl formamide or ethanol. The coupling procedures were carried out at 4° C. over 6 hours by syringe drive. The coupled proteins were dialyzed against buffer to remove uncoupled photoreactive groups. Each protein responded differently to the coupling procedure conditions so modifications of the ratios of photogroup-NOS to protein and the buffer systems providing the greatest coupling efficiencies and stabilities of the proteins were chosen.

Synthesis of Photoactivatable Polymeric Spacers. Photoactivatable derivatives of hydroxyl terminal polyethylene glycols (PEG) of molecular weights 1000, 1450 and 3350 were prepared by a modification of the phase-transfer method of Kimura et al, cited above. The phase-transfer method of ANP-PEG synthesis consists of using 60% aqueous KOH/toluene with fluoronitroazidobenzene and PEG, followed by extraction and thin layer chromatographic purification.

The N-oxy-succinimide esters of ANP-EAC and BBA were added in 0.5× amounts to 1× Jeffamine in very dry Gold Label Solvents, dry dimethyl formamide or dioxane. After 16 hours of reaction at room temperature in the dark, the products were isolated by TLC in 85/15/1/1 chloroform/methanol/H$_2$O/acetic acid. The mono-substituted Jeff derivatives were extracted with the thin layer chromatography solvent and azeotrophed with H$_2$O to remove the residual acetic acid. The water solute products ANP-EAC-JEFF and BBA-JEFF were isolated at 15% and 10% yields, respectively.

Photocoupling Hydrophilic Spacers to Insoluble Supports

Microtiter plates. Solutions of derivatized hydrophilic spacers containing 100-3000 ng of spacer were added to the wells of polyvinyl chloride and polystyrene 96-well microtiter plates. The solutions were left to adsorb and evaporate to dryness. (Some assistance was provided by placing the plates in a 70° C. oven for 1 hour, followed by adsorption under a continuous air-flow hood.) The hydrophilic spacers were then covalently coupled to the supports by photolysis. The supports were placed 10 cm from an appropriate high intensity lamp at 4° C. for 12 hours. The noncovalently coupled spacers were then washed away with phosphate-buffered saline (PBS).

Sephadex Gels. A 20 mg portion of Sephadex G-25-150 (Bead size 50-150 um) was placed in a siliconized 12×75 mm borosilicate glass tube. 100-3000 ng of photoactivatable hydrophilic spacer was added to each tube. The solutions were left to adsorb to dryness. The time required for this process was reduced by placing the plates in a 70° C. oven for 1 hour, followed by adsorption under a continuous air-flow hood. The hydrophilic spacers were covalently coupled to the supports by photolysis. The tubes containing the gels were placed 10 cm from the appropriate high intensity lamp at 4° C. for 12 hours. The non-covalently coupled spacers were then washed away with phosphate-buffered saline (PBS).

After photocoupling the derivatized hydrophilic spacers to insoluble supports, the biomolecules of interest (polyclonal antibodies against open-ring penicillin, human gamma globulin and monoclonal antibodies raised against HGG, and human alphafetoprotein and monoclonal antibodies raised against this tumor-associated antigen) were linked to the spacers by protein-protein coupling procedures. Two procedures were employed. Epsilon amino groups of biomolecules were coupled to terminal amino groups of spacers with glutaraldehyde. Carboxyl groups of biomolecules were coupled to spacer amino groups with a water-soluble carbodiimide, 1-ethyl-3-(3-dimethylamino propyl) carbodiimide HCl (EDC).

Assessing Polyclonal Antibodiy Activities. Fractionated rabbit polyclonal antiserum was radiolabeled. The amounts of antibody coupled to the matrices by passive adsoprtion and via glutaraldehyde or EDC coupling through hydrophilic spacers were quantitated by liquid scintillation spectrometry. The activities of the immobilized antibodies were assessed by addition of [$^{14}$C] penicillin. The total (pmole [$^{14}$C]Pen) and specific activities (pmole [$^{14}$C]Pen/pmole immobilized anti-Pen) were determined by direct coupling and immobilization through hydrophilic spacers.

Assessing Model Monoclonal Antibody Activities. The model pair of MGG and monoclonal anti-HGG was chosen for these tests. Radiolabeled HGG was coupled directly and through hydrophilic spacers to determine amounts of coupled antigen. Then, to assess immunoreactivities, non-radiolabeled HGG was coupled by these methods. Next, radiolabeled anti-HGG was added to the immogilized HGG. The immunoreactivities were assessed by liquid scintillation spectrometry. The ratios of pmole anti-HGG/pmole HGG were compared for direct coupling and immobilization through hydrophilic spacers.

Tables 11 and 12 illustrate the efficiency of coupling photoreactive spacers to polystyrene microtiter plates and to Sephadex gel.

TABLE 11

Efficiencies of Coupling Photoreactive Spacers to Polystyrene Microtiter Plates*.

| Sample | ng Applied | Mean ng Coupled/Well | % Coupled |
|---|---|---|---|
| ANP-BSA | 454.4 + 14.1 | 409.5 + 8.6 | 83.5 + 1.7 |
| BBA-BSA | 393.4 + 10.4 | 309.5 + 11.6 | 76.5 + 2.9 |
| ADDP-BSA | 438.0 + 14.1 | 281.0 + 5.6 | 72.2 + 0.8 |
| ANP-OVO | 703.7 + 27.1 | 662.6 + 30.1 | 94.8 + 4.8 |
| BBA-OVO | 364.0 + 12.6 | 194.6 + 19.9 | 55.4 + 4.7 |
| ANP-RN | 533.5 + 84.0 | 474.5 + 13.0 | 91.6 + 2.78 |
| BBA-RN | 466.8 + 42.2 | 338.8 + 18.0 | 72.6 + 3.8 |
| ANP-JEFF | 785.5 + 20.9 | 75.9 + 0.9 | 9.5 + 1.3 |
| BBA-JEFF | 466.1 + 42.5 | 48.6 + 3.8 | 10.5 + 0.8 |

*The values are representations from the compiled data of two experiments.

TABLE 12

Efficiencies of Coupling Photoreactive Spacers to Sephadex G-150-120

| Sample | ng Spacer Added | Mean ng Spacer Coupled 20 mg Gel | % Spacer Coupled to 20 mg Gel |
|---|---|---|---|
| BSA | 248.8 ± 8.15 | 8.39 ± 1.23 | 3.38 ± 0.49 |
| ANP-BSA | 253.91 ± 14.96 | 16.89 ± 3.65 | 6.65 ± 1.44 |
| BBA-BSA | 132.01 ± 2.00 | 12.06 ± 2.32 | 9.14 ± 1.76 |
| ADDP-BSA | 224.17 ± 8.15 | 13.76 ± 3.17 | 6.13 ± 1.41 |
| RN | 270.7 ± 2.03 | 18.28 ± 2.22 | 6.75 ± 0.82 |
| ANP-RN | 180.15 ± 1.93 | 20.64 ± 1.30 | 11.46 ± 0.72 |
| BBA-RN | 245.45 ± 2.02 | 13.91 ± 0.99 | 5.67 ± 0.40 |
| OVO | 224.3 ± 1.13 | 18.34 ± 1.49 | 8.17 ± 0.66 |
| ANP-OVO | 136.3 ± 1.01 | 8.78 ± 0.88 | 6.44 ± 0.64 |
| BBA-OVO | 60.90 ± 0.39 | 7.17 ± 0.56 | 11.76 ± 0.91 |
| ANP-JEFF* | 721.75 ± 17.92 | 13.49 ± 2.74 | 1.87 ± 0.38 |
| | 385.50 ± 6.18 | 7.92 ± 1.57 | 2.05 ± 0.41 |
| BBA-JEFF | 683.17 ± 13.02 | 43.27 ± 3.23 | 6.33 ± 0.47 |

TABLE 12-continued

Efficiencies of Coupling Photoreactive Spacers to Sephadex G-150-120

| Sample | ng Spacer Added | Mean ng Spacer Coupled 20 mg Gel | % Spacer Coupled to 20 mg Gel |
|---|---|---|---|
| | 321.21 ± 7.99 | 27.78 ± 2.01 | 8.65 ± 0.62 |

*Negligible amounts of Jeffamine non-specifically adsorbed to the gels.

The activities of passively adsorbed biomolecules were compared to the activities of biomolecules immobilized through the hydrophilic spacers, and Table 13 below summarizes the results of coupling anti-penicillin polyclonal antibodies to polystyrene microtiter plates. Use of the long chemical chain hydrophilic spacers provided the antibodies with substantially greater specific activities in comparison to the adsorption of antibodies to the microtiter plate or the direct coupling of the antibodies to the plate.

TABLE 13

Specific Activities of Anti-Penicillin Polyclonal Antibodies Immobilized on Polystyrene Microtiter Plates Derivatized with Hydrophilic Spacers

| Spacer | Coupler | ng Antibody Bound | pmole Pen Bound | pmole Pen/ug Antibody | Total Activity Ratio[1] | Specific Activity Ratio[2] |
|---|---|---|---|---|---|---|
| None | Adsorb | 510.97 ± 9.33 | 16.15 ± 0.39 | 32.31 ± 1.55 | 1.00 | 1.00 |
| None | ANP | 364.04 ± 20.78 | 20.60 ± 1.45 | 56.58 ± 3.99 | 1.28 | 1.75 |
| None | BBA | 491.74 ± 20.95 | 21.39 ± 2.00 | 43.49 ± 4.07 | 1.32 | 1.34 |
| ANP-BSA | EDC | 143.43 ± 7.05 | 27.56 ± 2.40 | 200.33 ± 4.73 | 1.71 | 6.19 |
| BBA-BSA | EDC | 101.24 ± 8.12 | 31.26 ± 1.25 | 308.79 ± 12.37 | 1.94 | 9.56 |
| ANP-OVO | EDC | 173.62 ± 15.32 | 19.48 ± 0.89 | 112.24 ± 5.13 | 1.21 | 3.47 |
| BBA-OVO | EDC | 148.36 ± 20.55 | 20.91 ± 1.81 | 140.98 ± 12.23 | 1.29 | 4.36 |
| ANP-RN | EDC | 155.24 ± 15.24 | 31.88 ± 1.42 | 205.40 ± 9.17 | 1.97 | 6.36 |
| BBA-RN | EDC | 129.12 ± 7.53 | 28.46 ± 2.43 | 220.46 ± 18.89 | 1.76 | 6.82 |
| ANP-JEFF | EDC | 139.73 ± 7.73 | 11.80 ± 0.63 | 84.44 ± 4.53 | 0.73 | 2.61 |
| BBA-JEFF | EDC | 94.02 ± 3.20 | 16.65 ± 0.97 | 177.08 ± 10.38 | 1.03 | 5.48 |

[1]Total Activity Ratio is the pmole Pen Bound divided by the pmole Pen Bound in the adsorbed only wells.
[2]Specific Activity Ratio is the pmole Pen/microgram Antibody divided by the same ratio of the adsorbed only antibody wells.

Table 14, below, provides data from the comparisons of the activities of the immobilized model antigen, HGG, on Sephadex gel. The specific activities of the immunoreactive pair (ng Anti-HGG/ng HGG) was improved substantially through the use of the spacers.

TABLE 14

Specific Activities of Monoclonal Anti-HGG Antibodies Immobilized on Sephadex Gels

| Spacer | Coupling | ng HGG Bound | ng Anti-HGG Bound | ng Anti-HGG/ng HGG × 100 |
|---|---|---|---|---|
| None | Adsorbed | 272.8 + 24.0 | 11.92 + 1.1 | 4.37 |
| None | DEAE | 1674.4 + 33.2 | 135.02 + 20.6 | 8.06 |
| ANP-BSA | Glut | 191.8 + 7.7 | 135.42 + 1.8 | 70.60 |
| ANP-BSA | EDC | 173.1 + 5.5 | 55.90 + 1.95 | 32.28 |
| ANP-JEFF | Glut | 126.4 + 10.7 | 52.08 + 3.53 | 41.20 |
| ANP-JEFF | EDC | 50.0 + 12.7 | 43.50 + 5.47 | 86.95 |

Table 15 shows the covalent coupling of HGG to a polyethylene glycol spacer bearing, at one end, a photogroup (ANP) and at the other a thermal group (NOS), the spacer being covalently bonded to a polyvinyl chloride microtiter plate through activation of the photogroup. Of interest, the data indicates that the ANP-PEG spacers themselves greatly reduce the amount of non-specific adsorption of HGG to the microtiter plates, indicating that plates having spacers covalently bound thereto allow facile specific coupling of biomolecules to the supports while reducing non-specific adsorption of the biomolecules.

TABLE 15

Coupling of HGG to ANP-PEG-NOS Derivatized Polyvinyl Chloride Microtiter Plates

| Spacer | Coupler | ng HGG Applied/Well | ng HGG Bound/Well |
| --- | --- | --- | --- |
| None | Adsorb | 50 | 4.51 + 0.36 |
| ANP-PEG | None | 50 | 0.25 + 0.08 |
| ANP-PEG | NOS | 50 | 9.64 + 0.39 |
| None | Adsorb | 2000 | 24.90 + 1.30 |
| ANP-PEG | None | 2000 | 6.45 + 0.08 |
| AP-PEG | NOS | 2000 | 39.65 + 1.87 |

While a preferred embodiment of the present invention has been described, it should be understood that various changes, adaptations and modifications may be made therein without departing from the spirit of the invention and the scope of the appended claims.

What is claimed is:

1. A spacer for attaching a biomolecule to a support having a hydrophobic surface, the spacer comprising a hydrophilic chemical chain carrying a relatively hydrophobic guiding group capable of becoming embedded in the hydrophobic surface, the spacer being capable of covalently bonding to a biomolecule, the spacer further comprising a stopping group, along the length of the spacer, the stopping group being relatively hydrophilic to the guiding group and to the hydrophobic surface of the support, the stopping group being positioned between the bulk of the hydrophilic chain and the hydrophobic guiding group, wherein the guiding group is derived from an aminoalkyl carboxylic acid.

2. A spacer according to claim 1 wherein the aminoalkyl carboxylic acid is selected from the group consisting of omega aminoundecanoic acid, epsilon amino caproic acid, gamma aminobutyric acid, and beta-alanine.

3. A spacer and biomolecule combination for attaching the biomolecule to a support having a hydrophobic surface, the spacer comprising a hydrophilic chemical chain carrying a relatively hydrophobic guiding group capable of becoming embedded in the hydrophobic surface, the spacer having the biomolecule covalently bound thereto, the spacer further comprising a stopping group, along the length of the spacer, the stopping group being relatively hydrophilic to the guiding group and to the hydrophobic surface of the support, the stopping group being positioned between the bulk of the hydrophilic chain and the hydrophobic guiding group, wherein the guiding group is derived from an aminoalkyl carboxylic acid.

4. A spacer according to claim 3 wherein the aminoalkyl carboxylic acid is selected from the group consisting of omega aminoundecanoic acid, epsilon amino caproic acid, gamma aminobutyric acid, and beta-alanine.

5. A spacer according to claim 3 wherein the stopping group and the spacer are both provided by the same molecule.

6. A spacer according to claim 5 wherein the same molecule is albumin.

7. A combination of spacer and support having a hydrophobic surface, for attaching a biomolecule to the support surface, the spacer comprising a hydrophilic chemical chain carrying a relatively hydrophobic guiding group, the group being embedded in the hydrophobic surface of the support, the spacer being capable of covalently bonding to a biomolecule, the spacer further comprising a stopping group, along the length of the spacer, the stopping group being relatively hydrophilic to the guiding group and to the hydrophobic surface of the support, the stopping group being positioned between the bulk of the hydrophilic chain and the hydrophobic guiding group, wherein the guiding group is derived from an aminoalkyl carboxylic acid.

8. A combination of spacer, biomolecule, and support having a hydrophobic surface, comprising a spacer covalently bound to the biomolecule, thereby attaching the biomolecule to the support surface, the spacer comprising a hydrophilic chemical chain carrying a relatively hydrophobic guiding group, the group being embedded in the hydrophobic surface of the support, the spacer further comprising a stopping group, along the length of the spacer, the stopping group being relatively hydrophilic to the guiding group and to the hydrophobic surface of the support, the stopping group being positioned between the bulk of the hydrophilic chain and the hydrophobic guiding group, wherein the guiding group is derived from an aminoalkyl carboxylic acid.

9. A spacer according to claim 1 or 3 further comprising a latent reactive group adjacent the guiding group, the latent reactive group being capable of covalently attaching the spacer to the surface.

10. A spacer according to claim 9 wherein;

the latent reactive group is selected from the group consisting of aryl, alkyl, and acyl azides, oxazidines, isocyanates, alkyl and 2-ketodiazo derivatives and diazirines, aromatic ketones, and aromatic diazonium derivatives;

the guiding group is selected from the group consisting of omega aminoundecanoic acid, epsilon amino caproic acid, gamma aminobutyric acid, and beta-alanine;

the stopping group is selected from the group consisting of albumin, monosaccharides, polysaccharides, cysteic acid, gluconic acid, and taurine; and the spacer chain is selected from the group consisting of chains having repeating ethoxy or isopropoxy groups.

11. A spacer according to claim 10 wherein;

the latent reactive group is benzoyl benzoic acid;

the guiding group is omega aminoundecanoic acid;

the stopping group is cysteic acid; and the spacer chain is polyethylene glycol.

* * * * *